United States Patent [19]

Turner et al.

[11] Patent Number: 5,092,971
[45] Date of Patent: Mar. 3, 1992

[54] BROMINATION

[75] Inventors: Philip J. Turner, Widnes, England; Martin Jeff, Houston, Tex.

[73] Assignee: Interox Chemicals Limited, London, England

[21] Appl. No.: 326,109

[22] Filed: Mar. 20, 1989

[30] Foreign Application Priority Data

Mar. 19, 1988 [GB] United Kingdom ................ 8806584

[51] Int. Cl.$^5$ ............................................. C07C 17/00
[52] U.S. Cl. .............................. 204/157.99; 204/158.1
[58] Field of Search ....................... 204/157.97, 157.99, 204/158.1

[56] References Cited

U.S. PATENT DOCUMENTS 3,492,211 1/1970 Pochowicz ........................ 204/158.1
3,947,336 3/1976 Clark ................................ 204/157.7
4,165,268 8/1979 Marti ............................... 204/157.99
4,191,621 3/1980 Riethmann ....................... 204/157.99

FOREIGN PATENT DOCUMENTS 130416 2/1976 German Democratic Rep. .
118609 3/1976 German Democratic Rep. .

OTHER PUBLICATIONS

Kharasch et al, Journal of Organic Chemistry, vol. 3, pp. 33-47, 1938.

Primary Examiner—John Niebling
Assistant Examiner—Steven P. Marquis
Attorney, Agent, or Firm—Larson and Taylor

[57] ABSTRACT

Selective bromination of alkylarenes to the alpha monobrominated derivative is desirable as a precursor for the selective production of, for example, the corresponding alcohols. The product can be obtained by a photolytic reaction between the substrate, hydrogen peroxide and hydrogen bromide in approximately equimolar ratios in an organic solvent, but improvement in the yield of the product coupled with similar or improved selectivity in its production was either not achieved or was actually impaired by a range of variations in the ratios and by omitting the solvent.

The invention employs mole ratios of $H_2O_2$:substrate of 0.1:1 to 0.4:1, preferably 0.2:1 to 0.33:1 and of $H_2O_2$:bromide of 1:1.2 to 1:2, preferably about 1:1.3 to 1:1.8 and progressive introduction of the $H_2O_2$, either in the presence or absence of the solvent, while irradiating with light preferably having principal emissions in the range of 250 to 600 nm, and the process thereby achieves either or both of improved yield and improved selectivity of the alpha monobrominated product. The reaction mixture is preferably maintained at 50° to 70° C. The process is especially suitable for deactivated alkylarenes, such as o-nitrotoluene.

15 Claims, No Drawings

BROMINATION

The present invention relates to a process for the bromination of alkyl substituents of arenes and in particular to a process for the selective monobromination of such substituted arenes and especially those that contain additionally a deactivating substituent.

The inventors have recognised that it is possible to brominate an alkyl substituent of an arene at the alpha carbon atom, and especially methyl, by contacting the substrate with bromine whilst exposing the mixture to irradiation that is capable of generating free radicals of bromine. They have further recognised that bromine substitution on the alkyl substituent can take place, despite the presence around the arene nucleus of various other substituents, like nitro groups, which are capable of deactivating the substrate in respect of various substitution reactions, which accordingly might be expected to require more forcing conditions. The use of such forcing conditions means that the risk remains, despite the presence of a deactivating substituent, that plural bromine substitution can occur to a substantial extent and naturally a similar risk of plural bromination can obtain in the absence of a deactivating substituent.

There is a further factor that has to be taken into account when determining what conditions might be appropriate to try in order to obtain the monobrominated compound selectively and that factor is the competition that could be expected from ionic reactions. These reactions would cause substitution of arene hydrogen atoms and would be expected to increase in importance as the concentration of bromine is increased. Naturally, if more forcing conditions for a reaction are needed, increasing the concentration of reagents is a technique that springs to mind.

There has been a disclosure in East German Patent 130 416 to VEB Arzneimittelwerk Dresden that bromination of o-nitrotoluene can be carried out by first contacting the substrate (0.8 moles) with bromine (0.36 moles), irradiating the mixture with an infrared lamp providing heat and light, and when all the bromine had been consumed, generating further bromine in situ by gradual addition of hydrogen peroxide (0.36 moles) in order to continue the bromination process. Theoretically, such a procedure could result in the formation of 0.72 moles of monobrominated substrate, in the absence of any competetive reactions. The reactions were carried out in solution in carbon tetrachloride at reflux temperature of about 80° C. The yield of bromination product was 67% based on the bromine used and calculated as the monobromo product, which is about 0.48 moles. It can accordingly be deduced that the selectivity of the reaction was not very good, which suggests that other and competetive reactions were occurring to a very significant extent, for example resulting in the production of the corresponding dibrominated product.

The brominated reaction products are often not the final product, but are intermediates in the production of the corresponding alcohols, or possibly aldehydes or carboxylic acids. It would be highly desirable to produce the monosubstituted product more selectively in order to facilitate subsequent processing steps and alternatively or additionally reduce the expensive consumption of reagents in any non-desired side reactions. It will be recognised that this latter point is of considerable significance where the corresponding alcohol is the eventual product, since its direct production is convenient only from a monobrominated intermediate and not from a dibrominated intermediate.

In the course of the investigations that eventually resulted in the instant invention, it was found that conversion of about 75% of the deactivated substrate could be achieved, using mole ratios of substrate in an organic solvent, to hydrogen bromide and to hydrogen peroxide respectively of 1:1:1.1 under photolytic conditions, and this yielded nearly 70% of monobrominated product. The extent of conversion of the substrate could be increased by increasing the mole ratio of either bromide or hydrogen peroxide or both to the substrate, but in every case tried, this also resulted in a substantial impairment of the selectivity of the reaction to the monobrominated product. An understanding of the constraints upon the process was further hampered by the results of a trial using a molar excess of bromide, a 10% molar excess of hydrogen peroxide under otherwise the same process conditions except that no solvent was employed. In that trial, the extent of conversion fell dramatically to below 20% of the substrate, although with about 90% selectivity to the monobrominated species. By comparison, in the presence of solvent, over 90% conversion of the substrate had been achieved, but less than 80% selectivity. The inference that can be drawn is that impaired selectivity is the outcome of variations that improve substrate conversion and impaired conversion can occur in variations in which selectivity is maintained high.

It is an objective of the instant invention to define process conditions in which either of the aforementioned problems is ameliorated, that is to say that either the problem of impaired selectivity as conversion of the substrate is increased, or impaired conversion when the diluent/solvent is not employed, and in some embodiments, it is a further object of the invention to address both of the problems.

According to the present invention there is provided a process for brominating an alkylarene substrate employing a two phase reaction mixture comprising an aqueous phase and an organic phase, in which process the substrate forms the organic phase which optionally contains also a substantially non-reactive organic solvent, and the aqueous phase contains hydrogen bromide and into which hydrogen peroxide is introduced during a period of at least 10 minutes, the mole ratio of hydrogen peroxide to substrate being selected in the range of from 0.1:1 to 0.4:1, and the mole ratio of hydrogen peroxide to hydrogen bromide being selected in the range of 1:1.2 to 1:2, the reaction mixture being maintained at a temperature of from 20° to 80° C. and irradiated with light of a sufficiently high frequency to dissociate bromine into free radicals for a reaction period of at least 1 hour.

By the use of reaction conditions according to the present invention, there is achieved to some extent an improved balance in the process between the conflicting demands of vigorous reaction conditions with the intention of obtaining a good or better extent of reaction, i.e. conversion, and the continuing requirement to preserve to an acceptable extent high selectivity to monobrominated substrate.

The invention process is particularly suitable for the bromination at the alpha carbon atom in an alkyl substituent of benzene that is also substituted by at least one deactivating substituent such as cyano, sulpho and especially nitro substituents or is substituted by a fluoro, chloro, bromo or iodo group. The non-alkyl substituent may be in any position around the benzene nucleus relative to the alkyl substituent, including in particular the ortho position. The alkyl substituent is particularly suitably methyl. Thus, the present invention is described herein with particular reference to the bromination of ortho-nitrotoluene, but the conditions can be applied, with appropriate modifications, if needed, to the corresponding reactions employing the other substituted substrates.

One of the important characteristic features of the present invention process resides in the mole ratios of the reactants employed. The inventors found in the course of research into this class of reaction that the extent of bromination obtained is a function of the amount of bromine that is generated in situ. They recognised that the total amount of bromine that can be generated is governed by whichever of the two reactants of hydrogen peroxide and bromide is present in the lesser molar amount. Although for the generation of bromine the stoichiometric ratio is 1:2 for $H_2O_2$:HBr, the subsequent bromination of the substrate releases one mole of bromide per mole of substrate brominated, which can react with any residual hydrogen peroxide to regenerate half a mole of bromine. This cycle of bromine generation, consumption and regeneration can continue until all the hydrogen peroxide has been consumed or all the bromide has been substituted into the substrate, whichever occurs first. Thus, they recognised that the ratio of bromide to hydrogen peroxide can be varied within rather wide limits whilst still generating the same molar quantity of bromine in situ. This, they further recognised, enabled the mole ratio of bromine to substrate to be varied to some extent independently from the ratio of reactants that generated the bromine.

It was found that it is preferable for the present process to employ a deficiency of bromide in the reaction mixture relative to the hydrogen peroxide, i.e. a mole ratio of bromide to hydrogen peroxide of below 2:1, but not too great a deficiency, i.e. using a ratio above 1.2:1, and a convenient range is often about 1.35:1 to about 1.8:1. By employing such a mole ratio in conjunction with a substantial excess of substrate, it is possible to achieve an improved extent of reaction to the monobromide with a high degree of selectivity.

The reaction can be carried out either in the presence of an organic solvent which does not react to any significant extent with either hydrogen peroxide or bromine, such as chlorinated hydrocarbons, including specifically carbon tetrachloride, chloroform, methylene dichloride, ethylene dichloride, tetrachloroethylene and tetrachloroethane. A convenient amount of such solvents comprises up to three times the volume of substrate, i.e. v/v, though higher amounts of solvent are useable at reduced space yield. Conveniently, though, the reaction can be carried out in the absence of any other solvent. By so doing, it is possible to obtain a comparatively high yield of brominated product. It is preferable to employ a mole ratio of about 3:1 to 5:1 of substrate to hydrogen peroxide. This means that at the end of the reaction there remains a significant excess of unreacted substrate which is available for use in a subsequent reaction either after separation from the reaction product as such or after the latter has been converted to a derivative such as the corresponding alcohol.

Temperature is a factor of some importance in the reaction. It has been found that an increase in temperature tends to increase the rate and extent of conversion of the substrate, but it also results in a significantly greater production of unwanted side-products. Thus, an increase in temperature reduces the selectivity of the reaction away from the desired monobrominated product. By adopting the other reaction conditions and in particular the combination of high substrate to hydrogen peroxide and deficient bromide to hydrogen peroxide, it has been found possible to mitigate or ameliorate the unwanted effect of increased temperature, and thereby enable high selectivity to the monobrominated product to be achieved even at temperatures at the higher end of the range of possible temperatures, i.e. at 50° C. or more. The most convenient temperature range is from about 60° to about 70° C.

The radiation illuminating the reaction has as its object the dissociation of bromine into bromine radicals. Thus, the effective radiation has a wavelength of not more than 600 nm. A significant proportion of useful radiation is available from lamps which have principal emissions in the range of 600 to 250 nm. Lamps which are described as daylight lamps have been found particularly suitable for the instant invention since the greater part of their radiation is emitted within the preferred wavelength range. Suitable lamps are often desribed as high pressure sodium discharge lamps (SON), mercury fluorescent lamps (MBF) and tungsten or tungsten halogen lamps. UV light is preferably filtered out. It will be recognised that there is a relationship between effective radiation intensity and reaction rate and consequeently also with reaction period, the more intense the radiation, the faster the rate and shorter the reaction period needed to achieve the desired generation and utilisation of the bromine reactant.

It will also be understood that the actual design of the apparatus employed will contribute significantly to effectiveness of employment of the radiation, including external factors such as the ratio of reaction volume to illuminated surface area. Radiation lamps can for example be positioned above the surface of the reaction mixture and/or immersed within it. Alternatively or additionally the vessel wall can be provided with translucent ports through which the radiation is shone into the reaction mixture. Reflectors can be used to minimise radiation losses. By way of guidance only, on a laboratory scale, we have found that a daylight spectrum lamp having a nominal luminous flux of 8,500 lumens set at a distance of about 20/25 cms from the reaction vessel, permits the reaction to progress to completion within a period normally from about 2 to about 3 hours after the hydrogen peroxide has been introduced.

It is of practical importance to take into account internal factors that affect the efficiency of utilisation of the radiation employed, when designing more suitable reaction vessels for this reaction. These factors include the ratio of reaction volume to illuminated surface area and the maximum effective path length of the radiation in the reaction mixture, which will itself correlate with the concentrations of light absorbers in the mixture. The interaction between the two factors determines the proportion of reaction volume that is effectively illuminated at any time. As the proportion falls away from 100% of the volume, the reaction time tends to lengthen. The actual design of the reaction vessel is within the control of the process operator and in preference the apparatus will be selected or modified so as to minimise or eliminate volumes of reaction mixture that are not penetrated by the radiation directly, or will employ preferably efficient mixing of the reaction mixture so as to increase the likelihood of all the reaction mixture containing bromine and substrate passing frequently through an illuminated zone of the reaction vessel.

The total reaction period for the reaction normally comprises two parts, namely the period of introduction of the hydrogen peroxide and secondly the post-introduction period. The ratio between the two parts can be varied widely, but it is convenient to employ an introduction period in the region of 10 to 120 minutes during which period peroxide is introduced continuously or in small amounts quite regularly, although a longer period of introduction can be used if desired, in which case the post-introduction period would usually be correspondingly shorter. The control of the rate of bromine production, which occurs as a direct result of progressive introduction of the hydrogen peroxide, means that there is control of the concentration of bromine in the reaction mixture to levels that are substantially lower than would be the case if all the bromine were introduced as such. In consequence, the invention process is able to avoid to a considerable extent the physical bromine losses that could otherwise result from a prolonged reaction period at elevated temperatures, and additionally circumvents excessive retardation of the reaction that could arise from the presence of the equimolar amount of bromine per mole of substrate in the reaction mixture that would be needed to obtain the monobromo compound. The reaction is normally continued until all the bromine generated in situ has been consumed, which is shown by a loss or change of colour in the reaction mixture. In many instances, the total reaction period lasts from 2 to 8 hours, depending at least in part upon the temperature employed.

The product can subsequently be separated from the excess starting material and by-products, for example by removing solvent, if present, under vaccuum, and by crystallisation and/or recrystalisation methods. As an alternative, for at least some products, the monobrominated product can be further reacted, such as by hydrolisis to the corresponding alcohol before separation and/or product purification is carried out.

Having described the invention in general terms, specific embodiments thereof will now be described more fully by way of example only.

COMPARISONS CA to CE and EXAMPLES 1 to 4

In these Comparisons and Examples, the same apparatus and same experimental method was employed, and at the same scale, 1 unit of the reagents in the Table representing 0.2 moles, the principal variations between the runs being the ratios of reactants employed, and the presence or absence of a non-reactive organic diluent in the reaction medium. The relevant conditions for each variation are summarised in the Table below.

The apparatus comprised a multi-necked 500 ml glass-flask equipped with stirrer, thermometer, reflux condenser and inlet port for the introduction of reagents, held in a water-bath to effect temperature control. The flask was illuminated by a daylight spectrum lamp, specifically a Thorn A1/258 24 volt 250 watt lamp having nominal luminous flux of 8,500 lumens that was positioned at a distance of about 20 cms away from the flask.

The experimental method comprised introducing all the ortho-nitro toluene, referred to as ONT in the Table and all the non-reactive diluent, chloroform 100 mls, when it was employed, into the flask, introducing all the hydrogen bromide as a 62% w/w solution in water, heating the mixture to the desired reaction temperature, 60° C. and thereafter introducing aqueous hydrogen peroxide in the form of 65% w/w solution gradually over a period of about 1 hour. The reaction mixture was maintained at the reaction temperature and well-stirred until the red colour from bromine that was generated in situ by reaction between the hydrogen bromide and hydrogen peroxide had been consumed. The overall total reaction time was usually from 2 hours to 5 hours. The reaction mixture was then cooled and the illumination extinguished to halt the reaction and side reactions, and solid products, if any, separated off.

The mixture was analysed by GLC to determine the extent of consumption of ONT in moles referred to as Cons ONT in the Table and likewise the products to determine the yield of the desired product, ortho-nitro benzyl bromide espressed as yield mono in the Table and by-products. When only 1 unit of ONT was present, as in Comparisons CA to CD, the figure given in the selectivity column in the Table is the ratio of the two preceding columns, expressed as a percentage. In the subsequent Comparison CE and Examples, the substrate represented at least a substantial part of the organic phase of the reaction medium, and accordingly the separation of the solid products entrained physically a measurable amount of substrate therein, which had not been reacted chemically and was capable of subsequent recovery and separation therefrom. The recorded figure for consumption is therefore significantly greater than the amount that has been converted. Accordingly, and to avoid a misleadingly poor impression for those processes, the figures for selectivity are prefixed by *, and are expressed as the ratio of monobrominated product to the dibrominated by-product.

TABLE

| Ex/ Comp | Mole ratio Reactants | | | Solvent | Cons. ONT moles | Yield mono moles | Select % |
| --- | --- | --- | --- | --- | --- | --- | --- |
| | HBr | H$_2$O$_2$ | ONT | | | | |
| CA | 1 | 1.1 | 1 | + | .151 | .140 | 92.4 |
| CB | 1 | 1.5 | 1 | + | .164 | .143 | 87.9 |
| CC | 2 | 1.1 | 1 | + | .185 | .142 | 79.8 |
| CD | 2 | 1.1 | 1 | − | .036 | .034 | 90 |
| CE | 1.5 | 1.1 | 2 | + | .238 | .140 | *93/7 |
| 1 | 1.5 | 1.1 | 3 | + | .248 | .176 | *97/3 |
| 2 | 1.5 | 1.1 | 4 | + | .213 | .178 | *96/4 |
| 3 | 1.5 | 1.1 | 4.65 | − | .230 | .178 | nm |
| 4 | 2 | 1.1 | 4.65 | − | .221 | .169 | *98/2 |

From the Table, it can be seen that the yield of monobrominated product remained obstinately at about 0.14 moles in all of comparisons CA to CE, when unreactive diluent, chloroform, was present. This was so when using approximately stoichiometric amounts of HBr, H$_2$O$_2$ and ortho-nitro toluene, or when employing excess HBr or excess H$_2$O$_2$, or when employing a similar excess of ortho-nitro toluene. If the result obtained in the absence of solvent in comparison CD is studied, it will be seen that the extent of conversion of the ortho-nitro toluene was extremely poor in comparison with the result in the similar, but solvent-employing comparison CC. The inference that can be drawn is that it is deleterious to omit the solvent. The second inference that could reasonably be drawn is that when the organic diluent was present, the observed effects from changing the ratios of the three reagents tend to be self-cancelling. Thus, for example, increasing the ratio of hydrogen peroxide to the other two reagents lead to an increase in the conversion of the ortho nitro toluene but simultaneously lead also to a reduction in the desired selectivity of the reaction and the two combined resulted in virtually the same amount of monobrominated product being obtained. A similar analysis can be given for the variations in which the ratios of respectively bromide and ortho nitrotoluene to the other reagents was each increased. Self-evidently, these comparison processes do not point the way to enhanced selectivity and/or yield of production of the monobrominated product.

However, it can also be seen from the Table that when the ratio of ortho-nitro toluene to the other reactants was substantially increased to 3:1 or higher, it was possible to obtain a significant improvement in the yield of monobrominated product from 0.14 moles to 0.18 moles, a gain of nearly 30% of the base yield, whilst still retaining a high degree of selectivity as can be seen by comparing the molar ratio of mono and di brominated products. Moreover, it is evident that at such high excesses of ortho-nitro toluene, it is able to act as its own reaction medium without undue impairment of the conversion of the ortho-nitro toluene to product. When Example 3 was repeated, under otherwise identical conditions, the yield of the desired monobrominated product was 0.183 moles and the selectivity was 95:5 for the ratio of monobrominated to dibrominated products. From a comparison between Examples 3 and 4, it can be seen that the yield of monobrominated product was better at the lower mole ratio of HBr:H$_2$O$_2$ of 1.5:1.1 than at the somewhat higher ratio of 2:1.1, but that the best selectivity expressed as ratio of mono:di products was obtained at that higher reactants ratio to hydrogen peroxide of 2:1.1. This latter observation is itself somewhat surprising, in that the skilled man might expect that such an increase in the amount of hydrogen bromide would favour the more highly brominated product and accordingly confirms the unexpected nature of the invention.

We claim:

1. A process for brominating an alkylarene substrate employing a two phase reaction mixture comprising an aqueous phase and an organic phase, in which process
   a) the organic phase comprises the substrate and optionally contains also a substantially non-reactive organic solvent,
   b) the aqueous phase contains hydrogen bromide and generates bromine from the hydrogen bromide,
   c) hydrogen peroxide is introduced during a period of at least 10 minutes into the reaction mixture,
   d) the mole ratio of hydrogen peroxide to substrate is selected in the range of from 0.1:1 to 0.4:1,
   e) the mole ratio of hydrogen peroxide to hydrogen bromide is selected in the range of 1:1.2 to 1:2, and
   f) the reaction mixture is maintained at a temperature of from 20° to 80° C. and irradiated with light of a sufficiently high frequency to dissociate bromine into free radicals for a reaction period of at least 1 hour.

2. A process according to claim 1 in which the arene moiety in the alkylarene substrate is a benzene group, optionally substituted by a deactivating group.

3. A process according to claim 2 in which the arene moiety in the alkylarene substrate is substituted by a deactivating group selected from the group consisting of cyano, sulpho and nitro groups.

4. A process according to claim 3 in which the deactivating group is a nitro group.

5. A process according to claim 1 wherein the alkyl moiety in the alkylarene substrate is a methyl group.

6. A process according to claim 1 wherein the substrate is toluene substituted by a deactivating group selected from the group consisting of cyano, sulpho and nitro groups.

7. A process according to claim 1 wherein the reaction mixture is irradiated with light having principal emission in the wavelength range of 250 to 600 nm.

8. A process according to claim 1 or 6 wherein the mole ratio of substrate to hydrogen peroxide is selected in the range of 3:1 to 5:1.

9. A process according to claim 1 or 6 wherein the mole ratio of bromide to hydrogen peroxide is selected in the range of 1.3:1 to 1.8:1.

10. A process according to claim 1 or 6 wherein the reaction mixture is maintained at a temperature in the range of from 50° to 70° C.

11. A process according to claim 9 wherein said temperature range is from 60° to 70° C.

12. A process according to claim 1 or 6 wherein the reaction mixture contains either no substantially non-reactive organic solvent or up to 3 volumes of substantially non-reactive organic solvent per volume of substrate.

13. A process according to claim 12 characterised in that the solvent is selected from chlorinated hydrocarbons.

14. A process according to claim 1 or 6 wherein the hydrogen peroxide is introduced into the reaction mixture containing the bromide and substrate during a period of from 10 to 120 minutes.

15. A process according to claim 1 or 6 wherein the reaction period lasts from 2 to 8 hours.

* * * * *